(12) United States Patent
Shaver et al.

(10) Patent No.: US 9,340,481 B1
(45) Date of Patent: May 17, 2016

(54) PROCESS FOR FLASHING A REACTION MEDIUM COMPRISING LITHIUM ACETATE

(71) Applicant: Celanese International Corporation, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

(*) Notice: Subject to any disclaimer, the term of this patent is extended or adjusted under 35 U.S.C. 154(b) by 0 days.

(21) Appl. No.: 14/874,332

(22) Filed: Oct. 2, 2015

Related U.S. Application Data

(63) Continuation-in-part of application No. 14/789,006, filed on Jul. 1, 2015.

(60) Provisional application No. 62/080,035, filed on Nov. 14, 2014.

(51) Int. Cl.
*C07C 51/12* (2006.01)
*C07C 51/44* (2006.01)
*B01J 31/20* (2006.01)

(52) U.S. Cl.
CPC ............... *C07C 51/12* (2013.01); *B01J 31/20* (2013.01); *C07C 51/44* (2013.01)

(58) Field of Classification Search
CPC ...................................................... C07C 51/44
See application file for complete search history.

(56) References Cited

U.S. PATENT DOCUMENTS

| | | | |
|---|---|---|---|
| 3,791,935 | A | 2/1974 | Eubanks et al. |
| 4,008,131 | A | 2/1977 | Price |
| 4,792,620 | A * | 12/1988 | Paulik et al. ............... 560/232 |
| 5,001,259 | A | 3/1991 | Smith et al. |
| 5,416,237 | A | 5/1995 | Aubigne et al. |
| 5,516,735 | A | 5/1996 | Tanigawa |
| 5,625,095 | A | 4/1997 | Miura et al. |
| 5,723,660 | A | 3/1998 | Morimoto et al. |
| 6,303,813 | B1 | 10/2001 | Scates et al. |
| 6,657,078 | B2 | 12/2003 | Scates et al. |
| 7,476,761 | B2 | 1/2009 | Kojima |
| 7,820,855 | B2 | 10/2010 | Patt |
| 7,884,241 | B2 | 2/2011 | Miura et al. |
| 8,940,932 | B2 | 1/2015 | Shimizu |
| 8,957,248 | B2 | 2/2015 | Miura et al. |
| 9,006,483 | B2 | 4/2015 | Shimizu et al. |
| 9,073,843 | B2 | 7/2015 | Shimizu et al. |
| 9,115,071 | B2 | 8/2015 | Shimizu et al. |
| 2011/0288333 | A1 | 11/2011 | Shaver et al. |
| 2013/0264186 | A1 | 10/2013 | Shimizu et al. |
| 2013/0281735 | A1 | 10/2013 | Shimizu et al. |
| 2015/0299084 | A1 | 10/2015 | Shimizu et al. |
| 2015/0368176 | A1 | 12/2015 | Miura et al. |

FOREIGN PATENT DOCUMENTS

WO        2014/115826 A1        7/2014

OTHER PUBLICATIONS

Zaragoza Dorwald, Side Reactions in Organic Synthesis, 2005, WILEY-VCH Verlag GmbH & Co. KGaA, Weinheim, Preface. p. IX.*
Murphy et al, Inorganic Chimica Acta, 1985, 101, pp. L47-L49.*
Zhu, Y. et al. (Apr. 2009). "Techno-economic Analysis for the Thermochemical Conversion of Lignocellulosic Biomass to Ethanol via Acetic Acid Synthesis," prepared for U.S. Department of Energy, PNNL-18483, Pacific Northwest National Laboratory, Richland, WA, 79 pages.
Murphy, et al., 'Iodide and Acetate Promotion of Oxidative Addition of MeI to Rh(i) Carbonyl Complexes', *Inorganica Chimica Acta*, vol. 101, 1985, pp. L47-L49.
International Search Report received from the corresponding application No. PCT/US2015/053855, dated Jan. 21, 2016.

* cited by examiner

*Primary Examiner* — Paul A Zucker
(74) *Attorney, Agent, or Firm* — Kilpatrick Townsend & Stockton LLP

(57) ABSTRACT

A process for producing acetic acid is disclosed, in which the methyl iodide concentration is maintained in the vapor product stream formed in a flashing step. The process includes introducing a lithium compound into the reactor and maintaining a concentration of lithium acetate in the reaction medium is in an amount from 0.3 to 0.7 wt. %. The reaction medium is fed forward to the flashing step. The methyl iodide concentration in the vapor product stream ranges from 24 to less than 36 wt. %, based on the weight of the vapor product stream. The vapor product stream is distilled in a first column to obtain an acetic acid product stream comprising acetic acid and hydrogen iodide in an amount of less than or equal to 300 wppm and/or methyl iodide in an amount from 0.1 to 6 wt. %.

18 Claims, 1 Drawing Sheet

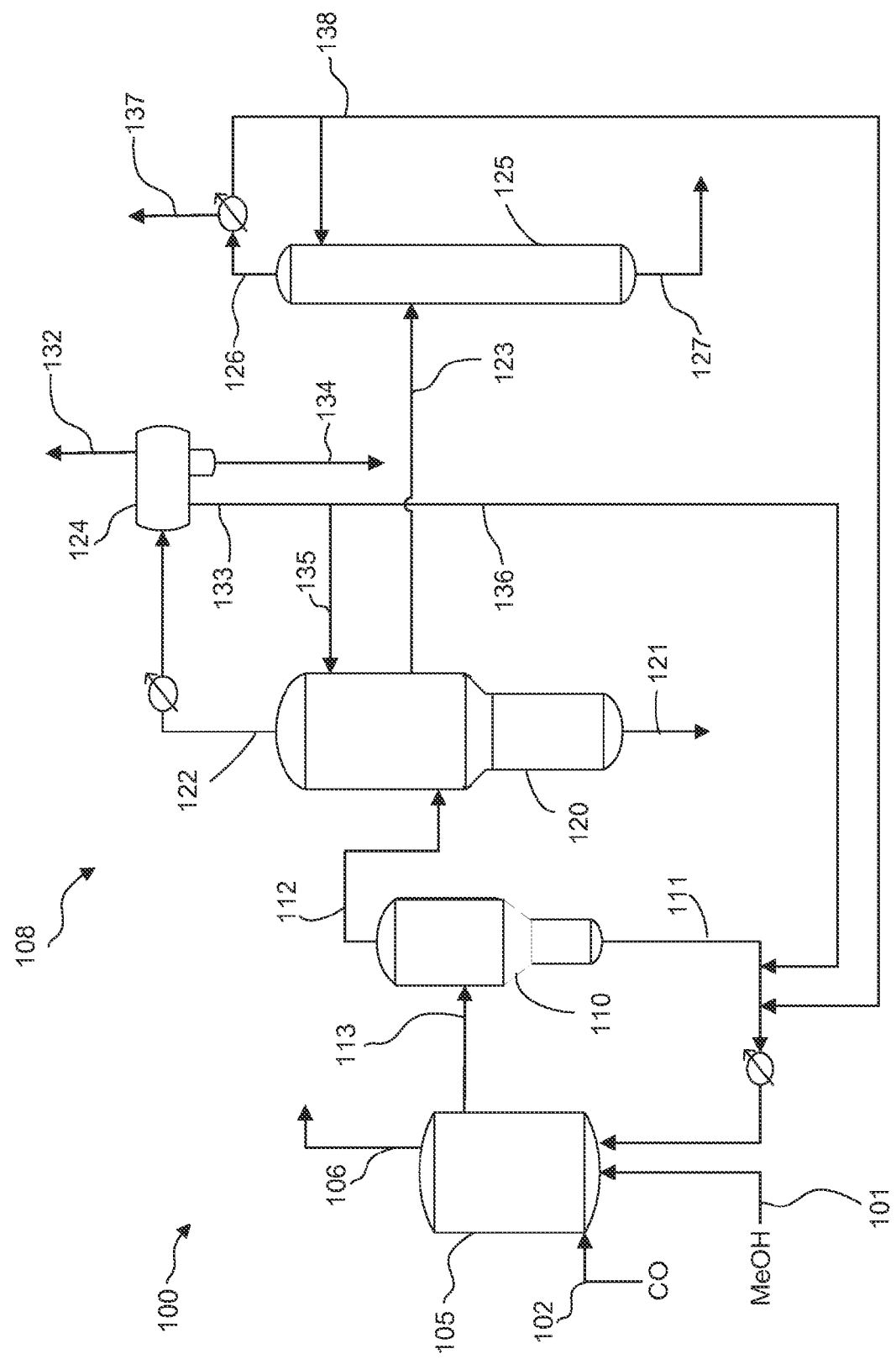

PROCESS FOR FLASHING A REACTION MEDIUM COMPRISING LITHIUM ACETATE

CROSS-REFERENCES TO RELATED APPLICATIONS

This patent application is a continuation-in-part and claims priority from U.S. patent application Ser. No. 14/789,006, entitled "Processes For Flashing A Reaction Medium," filed Jul. 1, 2015, and claims priority from U.S. Provisional Application No. 62/080,035, entitled "Processes For Producing Acetic Acid by Introducing a Lithium Compound," filed Nov. 14, 2014, the disclosure of which are incorporated herein by reference in its entirety.

FIELD OF THE INVENTION

This invention relates to processes for producing acetic acid and, in particular, to improved processes for flashing a crude acetic acid product in an acetic acid production system.

BACKGROUND OF THE INVENTION

Among currently employed processes for synthesizing acetic acid, one of the most useful, commercially, is the catalyzed carbonylation of methanol with carbon monoxide as taught in U.S. Pat. No. 3,769,329, which is incorporated herein by reference in its entirety. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. The reaction is conducted by continuously bubbling carbon monoxide gas through a liquid reaction medium in which the catalyst is dissolved.

Methanol and carbon monoxide are fed to a reactor as feedstocks. A portion of the reaction medium is continuously withdrawn and provided to a flash vessel where the product is flashed and sent as a vapor to a purification train. The purification train includes a light ends column which removes "light" or low boiling components as an overhead and provides a sidedraw stream for further purification. The purification train may further include columns to dehydrate the sidedraw stream or columns for removing "heavy" or high boiling components, such as propionic acid, from the sidedraw stream. It is desirable in a carbonylation process for making acetic acid to minimize the number of distillation operations to minimize energy usage in the process.

U.S. Pat. No. 5,416,237 discloses a process for the production of acetic acid by carbonylation of methanol in the presence of a rhodium carbonylation catalyst, methyl iodide and an iodide salt stabilizer by maintaining a finite concentration of water of up to about 10% by weight and a methyl acetate concentration of at least 2% by weight in the liquid reaction medium and recovering the acetic acid product by passing the liquid reaction medium through a flash zone to produce a vapor fraction which is passed to a single distillation column from which an acetic acid product is removed. The vapor fraction comprises water up to about 8% by weight, acetic acid product, propionic acid by-product and the majority of the methyl acetate and methyl iodide.

U.S. Pat. No. 7,820,855 discloses a carbonylation process for producing acetic acid including: (a) carbonylating methanol or its reactive derivatives in the presence of a Group VIII metal catalyst and methyl iodide promoter to produce a liquid reaction mixture including acetic acid, water, methyl acetate and methyl iodide; (b) feeding the liquid reaction mixture at a feed temperature to a flash vessel which is maintained at a reduced pressure; (c) heating the flash vessel while concurrently flashing the reaction mixture to produce a crude product vapor stream. The selection of the reaction mixture and the flow rate of the reaction mixture fed to the flash vessel as well as the amount of heat supplied to the flash vessel are controlled, such that the temperature of the crude product vapor stream is maintained at a temperature less than 90° F. cooler than the feed temperature of the liquid reaction mixture to the flash vessel, and the concentration of acetic acid in the crude product vapor stream is greater than 70% by weight of the crude product vapor stream. Through the flash vessel the product acetic acid and the majority of the light ends (methyl iodide, methyl acetate, and water) are separated from the reactor catalyst solution, and the crude process stream is forwarded with dissolved gases to the distillation or purification section in single stage flash. The methyl iodide concentrations decrease as the temperature of the flash vessel increases and the flow rates decrease.

U.S. Pat. No. 9,006,483 discloses a production process of acetic acid that seeks to inhibit the concentration of hydrogen iodide and provide a liquid-liquid separation of an overhead from a distillation column. Acetic acid is produced by distilling a mixture containing hydrogen iodide, water, acetic acid and methyl acetate in a first distillation column to form an overhead and a side cut stream or bottom stream containing acetic acid, cooling and condensing the overhead in a condenser to form separated upper and lower phases in a decanter. According to this process, a zone having a high water concentration is formed in the distillation column above the feed position of the mixture by feeding a mixture having a water concentration of not less than an effective amount to not more than 5% by weight (e.g., 0.5 to 4.5% by weight) and a methyl acetate concentration of 0.5 to 9% by weight (e.g., 0.5 to 8% by weight) as the mixture to the distillation column and distilling the mixture. In the zone having a high water concentration, hydrogen iodide is allowed to react with methyl acetate to produce methyl iodide and acetic acid.

The need remains for improved acetic acid production processes having improved separation steps, increased production capacities and lower operating costs.

SUMMARY OF THE INVENTION

In one embodiment, the present invention is directed to a process for producing acetic acid comprising carbonylating a reactant feed stream in the presence of water, rhodium catalyst, iodide salt and methyl iodide to form a reaction medium in a reactor. The reactant feed stream comprises methanol, methyl acetate, dimethyl ether, or mixtures thereof. The process further comprises introducing a lithium compound into the reactor, maintaining a concentration of lithium acetate in the reaction medium in an amount from 0.3 to 0.7 wt. %, separating the reaction medium in a flash vessel to form a liquid recycle stream and a vapor product stream, which comprises acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %. The process further comprises distilling at least a portion of the vapor product stream in a first column to obtain an acetic acid product stream comprising acetic acid and hydrogen iodide in an amount of less than or equal to 300 wppm, e.g., less than or equal to 50 wppm, and an overhead stream comprising methyl iodide, water and methyl acetate. In some embodiments, the vapor product stream may comprise acetaldehyde in an amount from 0.005 to 1 wt. %, e.g., preferably from 0.01 to 0.8 wt. % and more preferably from 0.01 to 0.7 wt. %. In a further embodiment, the vapor product stream may comprises acetic acid in an amount from 55 to 75 wt. %, methyl iodide in an amount from 24 to 35 wt. %, methyl acetate in an amount from 0.5 to 8 wt. %, water in an amount from 0.5 to 14 wt. %, and hydrogen iodide in an amount less than or equal to 0.5 wt. %. In another embodiment, the vapor product stream comprises acetic acid in an amount from 60 to 70 wt. %, methyl iodide in an amount from 25 to 35 wt. %, methyl acetate in an amount from 0.5 to 6.5 wt. %, water in an amount from 1 to 8 wt. %, and hydrogen iodide in an amount less than or equal to 0.1 wt. %. In some embodiments, the process further comprises venting a gaseous stream from the reactor that comprises hydrogen iodide in an amount of less than 1 wt. %, e.g., from 0.001 to 1 wt. %.

In one embodiment, the overhead stream is phase separated to form a light liquid phase and a heavy liquid phase. The light liquid phase may comprise acetic acid in an amount from 1 to 40 wt. %, methyl iodide in an amount of less than or equal to 10 wt. %, methyl acetate in an amount from 1 to 50 wt. %, water in an amount from 40 to 80 wt. %, acetaldehyde in an amount of less than or equal to 5 wt. %, and hydrogen iodide in an amount of less than or equal to 1 wt. %. In a preferred embodiment, the light liquid phase comprises acetic acid in an amount from 5 to 15 wt. %, methyl iodide in an amount of less than or equal to 3 wt. %, methyl acetate in an amount from 1 to 15 wt. %, water in an amount from 70 to 75 wt. %, acetaldehyde in an amount from 0.1 to 0.7 wt. %, and hydrogen iodide in an amount from 0.001 to 0.5 wt. %. In a further embodiment, a portion of the heavy liquid phase may be treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof.

In one embodiment, the liquid recycle stream comprises a metal catalyst in an amount from 0.01 to 0.5 wt. %, lithium iodide in an amount from 5 to 20 wt. %, corrosion metals in an amount from 10 to 2500 wppm, acetic acid in an amount from 60 to 90 wt. %, methyl iodide in an amount from 0.5 to 5 wt. %, methyl acetate in an amount from 0.1 to 5 wt. %, water in an amount from 0.1 to 8 wt. %, acetaldehyde in an amount from 0.0001 to 1 wt. %, and hydrogen iodide in an amount from 0.0001 to 0.5 wt. %.

In one embodiment, the lithium compound is selected from the group consisting of lithium acetates, lithium carboxylates, lithium carbonates, lithium hydroxides, and mixtures thereof. The concentration of methyl acetate in the reaction medium may be greater than the concentration of the lithium acetate. The process may further comprises maintaining a concentration of hydrogen iodide in the reaction medium from 0.1 to 1.3 wt. %. The reaction may be conducted while maintaining a carbon monoxide partial pressure from 2 to 30 atm and a hydrogen partial pressure in the reactor that is less than or equal to 0.04 atm.

In one embodiment, the acetic acid product stream may comprise methyl acetate in an amount from 0.1 to 6 wt. %, hydrogen iodide in an amount of less than or equal to 300 wppm, e.g., less than or equal to 50 wppm, the water concentration is maintained in the acetic acid product stream from 1 to 9 wt. %, and/or methyl iodide in an amount from 0.1 to 6 wt. %. the acetic acid product stream comprises each of the methyl iodide and the methyl acetate in an amount within the range of ±0.9 wt. % of the water concentration in the side stream. The acetic acid product stream may comprise each of the methyl iodide and the methyl acetate in an amount within the range of ±0.9 wt. % of the water concentration in the side stream.

BRIEF DESCRIPTION OF THE DRAWING

The present invention will be better understood in view of the appended non-limiting FIGURE, wherein:
FIG. 1 is a schematic drawing for producing acetic acid in accordance with the present invention.

DETAILED DESCRIPTION OF THE INVENTION

At the outset, it should be noted that in the development of any such actual embodiment, numerous implementation-specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure, such as a liquid distributor of a distillation column, include drain holes, drain tubes, drain slits, and the like, which allow a liquid to flow through the structure from one side to another. Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Vapor Product Stream

The production of acetic acid via the carbonylation of methanol involves the formation of a reaction medium in a reactor, and flashing the reaction medium in a flash vessel to form a liquid recycle stream and a vapor product stream. The vapor product stream is then distilled in one or more distillation columns to remove byproducts and form an acetic acid product. The present invention provides processes for producing acetic acid while reducing byproduct formation by maintaining a specific methyl iodide concentration in the vapor product stream formed in the flash step. Methyl iodide is a useful promoter for the carbonylation catalyst. During separation, however, methyl iodide tends to concentrate with the acetic acid that is separated from the reaction medium. Consequently, to avoid costly losses through fugitive emissions and to reduce iodide impurities in the acetic acid product, the methyl iodide must be separated from the acetic acid and returned to the reaction medium.

According to the present invention, methyl iodide concentrations are maintained at a sufficient level in the vapor product to support increased production rates while reducing the amount of methyl iodide that must be recovered from the vapor product stream. In one embodiment, the process may also comprise introducing a lithium compound into the reactor and maintaining a concentration of lithium acetate in the reaction medium in an amount from 0.3 to 0.7 wt. %. As described herein, it is advantageous to reduce methyl iodide in the reactor by maintaining these levels of lithium acetate. Reducing the methyl iodide in the reactor by using lithium acetate may advantageously control the methyl iodide in the vapor product stream in an amount from 24 to less than 36 wt. %.

Reducing the amount of methyl iodide advantageously debottlenecks the distillation columns due to the lower amounts of methyl iodide that must be separated. Debottlenecking the distillation columns advantageously increases production capacities and lowers operating costs. Maintaining methyl iodide at desired levels in the vapor product also beneficially keeps the hydrogen iodide concentrations in the downstream distillation columns at low levels and thus minimizes corrosion to the columns.

In one embodiment, the present invention is directed to a process for producing acetic acid comprising carbonylating a reactant feed stream in the presence of water, a rhodium catalyst, an iodide salt and a methyl iodide to form a reaction medium in a reactor. Said reactant feed stream comprises methanol, methyl acetate, dimethyl ether, or mixtures thereof. The process further comprises introducing a lithium compound into the reactor, maintaining a concentration of lithium acetate in the reaction medium in an amount from 0.3 to 0.7 wt. %, separating the reaction medium in a flash vessel to form a liquid recycle stream and a vapor product stream, which comprises acetic acid in an amount from 45 to 75 wt.

%, methyl iodide in an amount from 24 to less than 36 wt. %, methyl acetate in an amount of less than or equal to 9 wt. %, water in an amount of less than or equal to 14 wt. %, and distilling at least a portion of the vapor product stream in a first column to obtain an acetic acid product stream comprising acetic acid and hydrogen iodide in an amount of less than or equal to 300 wppm and an overhead stream comprising methyl iodide, water and methyl acetate.

As shown in U.S. Pat. No. 7,820,855, production rates decrease as methyl iodide concentrations decrease, based on mass flow rate from the reactor to the flash vessel. The present invention can maintain higher production rates without incurring the decrease in mass flow rate as described in U.S. Pat. No. 7,820,855. Methyl iodide at a concentration less than 24 wt. % results in undesirably low production rates. On the other hand, vapor product streams having methyl iodide at concentrations greater than or equal to 36 wt. % increase the load on the distillation columns needed to remove methyl iodide, which adversely impacts production capacity. Methyl iodide cannot be eliminated in the vapor product stream using the flash vessel and thus must be recovered through the distillation columns. Maintaining methyl iodide concentration in the range from 24 to less than 36 wt. % in the vapor product is important to control hydrogen iodide formation, which is resulted from the hydrolysis of methyl iodide. Hydrogen iodide is a known corrosion-causing compound and may undesirably concentrate with methyl iodide concentrations above 36 wt. %. in the vapor product stream. Thus, having a vapor product stream with 24 wt. % to less than 36 wt. % methyl iodide may provide the desired hydrogen iodide control.

The vapor product may be sampled using on-line measuring techniques to measure methyl iodide content and provide real-time or near real-time feedback. Sampling the vapor product stream on-line is easier than sampling the liquid reaction medium. In addition, the concentration of the methyl iodide in the vapor product is related to and provides an indirect indication of the concentration of methyl iodide in the reactor. The ability to maintain a consistent methyl iodide concentration in the vapor product stream is useful to set up a schedule for adding methyl iodide to the reactor. For example, in a commercial process, small amounts of methyl iodide are lost due to fugitive emissions and the use of various purge streams in the separation system. As the methyl iodide concentration in the vapor product decreases, additional methyl iodide may be added to the reactor. Conversely, when the methyl iodide concentration is too high, a portion of the heavy liquid phase from the light ends column may be purged from the system.

In addition to methyl iodide, the vapor product stream also comprises acetic acid, methyl acetate, and water. By-products such as hydrogen iodide, acetaldehyde, and propionic acid may also be present in the vapor product stream. The reactants, i.e., methanol and carbon monoxide, when not consumed, may be recovered in the vapor product stream. In one embodiment, the vapor product stream comprises acetic acid in an amount from 45 to 75 wt. %, methyl iodide in an amount from 24 to less than 36 wt. %, methyl acetate in an amount of less than or equal to 9 wt. %, and water in an amount of less than or equal to 14 wt. %, based on the total weight of the vapor product stream. More preferably, the vapor product stream comprises acetic acid in an amount from 55 to 75 wt. %, methyl iodide in an amount from 24 to 35 wt. %, methyl acetate in an amount from 0.5 to 8 wt. %, water in an amount from 0.5 to 14 wt. %, acetaldehyde in an amount from 0.01 to 0.8 wt. %, and hydrogen iodide in an amount less than or equal to 0.5 wt. %. In yet a further preferred embodiment, the vapor product stream acetic acid in an amount from 60 to 70 wt. %, methyl iodide in an amount from 25 to 35 wt. %, methyl acetate in an amount from 0.5 to 6.5 wt. %, water in an amount from 1 to 8 wt. %, acetaldehyde in an amount from 0.01 to 0.7 wt. %, and hydrogen iodide in an amount less than or equal to 0.1 wt. %.

The acetaldehyde concentration in the vapor product stream may be from 0.005 to 1 wt. %, e.g., from 0.01 to 0.8 wt. %, or from 0.01 to 0.7 wt. %, based on the total weight of the vapor product stream. In embodiments, the acetaldehyde may be present in amounts of less than or equal to 1 wt. %, e.g., less than or equal to 0.9 wt. %, less than or equal to 0.8 wt. %, less than or equal to 0.7 wt. %, less than or equal to 0.6 wt. %, or less than or equal to 0.5 wt. %, and/or the acetaldehyde may be present in amounts of greater than or equal to 0.005 wt. %, e.g., greater than or equal to 0.01 wt. %, greater than or equal to 0.05 wt. %, or greater than or equal to 0.1 wt. %. In addition to acetaldehyde, there may also be other permanganate reducing compounds ("PRC's"), such as acetone, methyl ethyl ketone, butylaldehyde, crotonaldehyde, 2-ethyl crotonaldehyde, 2-ethyl butyraldehyde, and the aldol condensation products thereof. In one embodiment, a suitable potassium permanganate test is JIS K1351 (2007). These compounds, if present in the vapor product stream, are generally in an amount similar to or less than the acetaldehyde concentrations. In one embodiment, is desirable to remove the PRC's, including acetaldehyde, to maintain low concentrations of PRC's in the vapor product stream. This may reduce the impurity/byproduct formation in the reactor.

The vapor product stream may comprise hydrogen iodide in an amount of less than or equal to 1 wt. %, based on the total weight of the vapor product stream, e.g., less than or equal to 0.5 wt. %, or less than or equal to 0.1 wt. %. In terms of ranges, hydrogen iodide may be present in amounts from 0.0001 to 1 wt. %, e.g., from 0.0001 to 0.5 wt. %, from 0.0001 to 0.1 wt. %. In some embodiments, when hydrogen iodide is controlled in the reactor, hydrogen iodide may be present in an amount of less than 0.0001 wt. %. These lower amounts are usually slightly above the detection limits.

The vapor product stream is preferably substantially free of, i.e., contains less than 0.0001 wt. %, propionic acid, based on the total weight of the vapor product stream.

In one embodiment, there is provided a process for producing acetic acid, comprising separating a reaction medium in a flash vessel to form a liquid recycle stream and a vapor product stream, which comprises acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %, acetaldehyde in an amount from 0.005 to 1 wt. %, and hydrogen iodide in an amount less than or equal to 1 wt. %. The process further comprises distilling at least a portion of the vapor product stream in a first column to obtain an acetic acid product stream comprising acetic acid and hydrogen iodide in an amount of less than or equal to 300 wppm and an overhead stream comprising methyl iodide, water and methyl acetate.

The present invention also advantageously facilitates maintaining a water balance in the separation system and, in particular, during the distillation steps by controlling the net production of water. As a result, the invention beneficially inhibits or prevents increases in water content that may necessitate the purging of water from the system. Purging of water can also adversely result in the loss of catalyst promoters such as methyl iodide. In exemplary embodiments, the net production of water in the distilling step increases by less than or equal to 0.5%, e.g., by less than or equal to 0.1% or by less than or equal to 0.05%, over the water concentration in the vapor product stream that is fed to the distilling step. In contrast, U.S. Pat. No. 9,006,483 describes promoting reactions that lead to the formation of water and allows for adding more water to the distilling step. Increases in the net production of water would be expected to be higher due to the promotion of these reactions and additions, leading to increased load on distillation equipment.

The vapor product stream is fed to a distillation column, e.g., a first column, which may also be referred to as a light ends column. In one optional embodiment, a portion of the vapor product stream may be condensed. The first column separates the vapor product stream to form an overhead stream, a product stream, and optionally a bottoms stream. The acetic acid product stream may be withdrawn as a sidedraw stream, and more preferably as a liquid sidedraw stream. In one embodiment, the acetic acid product stream primarily comprises acetic acid and may also comprise water, methyl iodide, methyl acetate, or hydrogen iodide. The acetic acid product stream withdrawn in the sidedraw preferably comprises acetic acid in an amount of greater than or equal to 90 wt. % acetic acid, based on the total weight of the sidedraw stream, e.g., greater than or equal to 94 wt. % or greater than or equal to 96 wt. %. In terms of ranges, the acetic acid product stream comprises acetic acid in an amount from 90 to 99.5 wt. %, e.g., 90 to 99 wt. %, or from 91 to 98 wt. %. Such concentrations allow a majority of the acetic acid fed to the first column to be withdrawn in the sidedraw stream for further purification. Although minor amounts of acetic acid may be present, acetic acid is preferably not recovered as a product in the overhead or bottoms of the first column.

The process preferably includes a step of maintaining a water concentration in the sidedraw stream in an amount from 1 to 9 wt. %, e.g., from 1 to 3 wt. %, and more preferably from 1.1 to 2.5 wt. %. In embodiments, the concentration of water in the side stream is maintained at greater than or equal to 1 wt. %, or greater than or equal to 1.1 wt. %, or greater than or equal to 1.3 wt. %, or greater than or equal to 1.5 wt. %, or greater than or equal to 2 wt. %, and/or in embodiments, the concentration of water in the side stream is maintained at less than or equal to 3 wt. %, or less than or equal to 2.8 wt. %, or less than or equal to 2.5 wt. %, or less than or equal to 2.1 wt. %. In embodiments, the concentration of hydrogen iodide in the side stream is maintained at less than or equal to 300 wppm, e.g., less than or equal to 275 wppm, less than or equal to 250 wppm, less than or equal to 225 wppm, less than or equal to 175 wppm, or less than or equal to 50 wppm, and/or in embodiments, the concentration of hydrogen iodide in the side stream is maintained at greater than or equal to 0.05 wppm, e.g., greater than or equal to 0.1 wppm, greater than or equal to 1 wppm, greater than or equal to 5 wppm, greater than or equal to 10 wppm or greater than or equal to 50 wppm. In terms of ranges, the sidedraw stream preferably comprises hydrogen iodide in an amount from 0.05 to 300 wppm, based on the total weight of the sidedraw stream, e.g., from 0.1 to 50 wppm, or from 5 to 30 wppm. Hydrogen iodide is soluble in acetic acid-water mixtures containing water in an amount from 3 to 8 wt. %, and the solubility of hydrogen iodide decreases as the water concentration decreases. This correlation results in increasing hydrogen iodide volatility, which leads to reduced amounts of hydrogen iodide being collected in the overhead of the column. Although hydrogen iodide has been indicated by others to be corrosive, a certain amount of hydrogen iodide under some conditions may beneficially act as a catalyst, such as a catalyst for forming dimethyl ether as described in U.S. Pat. No. 7,223,883 (describing the benefits of dimethyl ether formation in certain acetic acid separation processes), the entirety of which is incorporated herein by reference.

In addition to acetic acid and water, the sidedraw stream may also comprise one or more $C_1$-$C_{14}$ alkyl iodides in an amount from 0.1 to 6 wt. %, e.g., from 0.5 to 5 wt. %, from 0.6 to 4 wt. %, from 0.7 to 3.7 wt. %, or from 0.8 to 3.6 wt. %. In one embodiment, the one or more $C_1$-$C_{14}$ alkyl iodides comprise methyl iodide. Other alkyl iodides such as hexyl iodide may also be formed from carbonyl impurities such as acetaldehyde. More preferably, the sidedraw stream comprises one or more $C_1$-$C_{14}$ alkyl iodides in an amount from 0.5 to 3 wt. %. Due to the presence of water, the sidedraw stream may also contain methyl acetate in an amount from 0.1 to 6 wt. %, e.g., from 0.5 to 5 wt. %, from 0.6 to 4 wt. %, from 0.7 to 3.7 wt. %, or from 0.8 to 3.6 wt. %.

In one embodiment, a process is provided for producing acetic acid comprising separating a reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %, acetaldehyde in an amount from 0.005 to 1 wt. %, and hydrogen iodide in an amount less than or equal to 1 wt. %. The process further comprises distilling at least a portion of the vapor product stream in a first column to obtain an acetic acid product stream comprising acetic acid and methyl iodide in an amount from 0.1 to 6 wt. % and an overhead stream comprising methyl iodide, water and methyl acetate. The process preferably also includes a step of maintaining a water concentration in the sidedraw stream in an amount from 1 to 9 wt. %, e.g., from 1 to 3 wt. %. In one embodiment, the concentration of hydrogen iodide in the side stream is maintained at less than or equal to 300 wppm.

In one embodiment, a process is provided for producing acetic acid comprising separating a reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %, acetaldehyde in an amount from 0.005 to 1 wt. %, and hydrogen iodide in an amount less than or equal to 1 wt. %. The process further comprises distilling at least a portion of the vapor product stream in a first column to obtain an acetic acid product stream comprising acetic acid, and methyl acetate in an amount from 0.1 to 6 wt. %, and obtain an overhead stream comprising methyl iodide, water and methyl acetate. The process preferably also includes a step of maintaining a water concentration in the sidedraw stream in an amount from 1 to 9 wt. %, e.g., from 1 to 3 wt. %. In one embodiment, the concentration of hydrogen iodide in the side stream is maintained at less than or equal to 300 wppm.

In one embodiment, a process is provided for producing acetic acid comprising separating a reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %, acetaldehyde in an amount from 0.005 to 1 wt. %, and hydrogen iodide in an amount less than or equal to 1 wt. %. The process further comprises distilling at least a portion of the vapor product stream in a first column to obtain an acetic acid product stream comprising acetic acid, methyl iodide in an amount from 0.1 to 6 wt. %, and methyl acetate in an amount from 0.1 to 6 wt. %, and obtain an overhead stream comprising methyl iodide, water and methyl acetate. The process preferably also includes a step of maintaining a water concentration in the sidedraw stream in an amount from 1 to 9 wt. %, e.g., from 1 to 3 wt. %. In one embodiment, the concentration of hydrogen iodide in the side stream is maintained at less than or equal to 300 wppm.

As provided herein, in embodiments, there may be a stable amount of other reactor components and impurities, such as $C_1$-$C_{14}$ alkyl iodides, namely methyl iodide, and methyl acetate in the sidedraw stream based on the water concentration. By stable amount it is meant that the concentration of the one or more $C_1$-$C_{14}$ alkyl iodides and the concentration of methyl acetate is within the range of ±0.9 wt. % of the water concentration in the side stream, e.g., ±0.7 wt. %, ±0.6 wt. %, ±0.5 wt. %, ±0.4 wt. %, ±0.3 wt. %, ±0.2 wt. %, or ±0.1 wt. %. For example, when the water concentration is 2.5 wt. %, the concentration of $C_1$-$C_{14}$ alkyl iodides is from 1.6 to 3.4 wt. %, and the concentration of methyl acetate is from 1.6 to 3.4 wt. %. This may be achieved by controlling a recycle rate of a portion of the light liquid phase to the reactor. In some embodiments, controlling the recycle rate of a portion of the light liquid phase to the reactor may achieve a stable concentration of methyl iodide in the side stream of within the range of ±0.6 wt. % of the water concentration in the side stream, e.g., ±0.5 wt. %, ±0.4 wt. %, ±0.3 wt. %, ±0.2 wt. %, or ±0.1 wt. %.

In one embodiment, a process is provided for producing acetic acid comprising carbonylating a reactant feed stream in the presence of water, rhodium catalyst, iodide salt and methyl iodide to form a reaction medium in a reactor. The reactant feed stream comprises methanol, methyl acetate, dimethyl ether, or mixtures thereof. The process further comprises introducing a lithium compound into the reactor, maintaining a concentration of lithium acetate in the reaction medium in an amount from 0.3 to 0.7 wt. %, separating the reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. The process further comprises distilling at least a portion of the vapor product stream in a first column to obtain an acetic acid product stream comprising acetic acid and hydrogen iodide in an amount of less than or equal to 300 wppm and obtain an overhead stream comprising methyl iodide, water and methyl acetate. The acetic acid product stream comprises each of the methyl iodide and the methyl acetate in an amount ±0.9 wt. % of the water concentration in the side stream. In one embodiment, the vapor stream may also comprise acetaldehyde in an amount from 0.005 to 1 wt. %.

Maintaining the desired methyl iodide concentration in the vapor product stream is an improvement over other processes that focus on water and methyl acetate concentrations in the vapor product that feeds the first column, such as those described in U.S. Pat. No. 9,006,483. Unlike water and methyl acetate, methyl iodide has significant value and the loss of which can represent a substantial loss in cost. One of the advantages of the process disclosed herein is that it separates methyl iodide from the rest and returns it to the reactor, which allows for the recovery of this valuable catalyst promoter.

Hydrogen iodide concentration of the sidedraw stream is determined by potentiometric titration using lithium acetate as the titrant. Others have determined hydrogen iodide content indirectly by calculation. US Pub. No. 2013/0310603, for example, indicates that iodide ion concentration may be calculated by subtracting the iodide ion concentration derived from the iodide salt form (including iodides derived from co-catalysts and metal iodide) from the total concentration of iodide ion ($I^-$). Such indirect calculation techniques are typically inaccurate, resulting in a poor indication of actual hydrogen iodide concentration owing largely to the inaccuracies of the underlying ion measurement methods. In addition, this indirect calculation technique fails to account for other iodide forms because metal cations are measured and incorrectly assumed to be completely associated only with iodide anions while, in fact, the metal cations may be associated with other anions, such as acetate and catalyst anions. In contrast, the direct measurement of hydrogen iodide concentration according to the present invention advantageously reflects the actual hydrogen iodide concentration in the system, and can result in accuracy as low as 0.01%. In one embodiment, the hydrogen iodide concentration in the side stream may be determined by potentiometric titration using lithium acetate as the titrant.

Reaction Step

An exemplary reaction and acetic acid recovery system 100 is shown in FIG. 1. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof may be converted to methyl acetate in the liquid reaction medium by esterification with acetic acid.

Typical reaction temperatures for carbonylation may be from 150 to 250° C., with the range of 180 to 225° C. being preferred. The carbon monoxide partial pressure in the reactor may vary widely but is typically from 2 to 30 atm, e.g., from 3 to 10 atm. The hydrogen partial pressure in the reactor is typically from 0.05 to 2 atm, e.g., from 0.25 to 1.9 atm. In some embodiments, the present invention may be operated with a hydrogen partial pressure from 0.3 to 2 atm, e.g., from 0.3 to 1.5 atm, or from 0.4 to 1.5 atm. Because of the partial pressure of by-products and the vapor pressure of the contained liquids, the total reactor pressure may range from 15 to 40 atm. The production rate of acetic acid may be from 5 to 50 mol/L·h, e.g., from 10 to 40 mol/L·h, and preferably from 15 to 35 mol/L·h.

Carbonylation reactor 105 is preferably either a mechanically-stirred vessel, a vessel with an educted or pump-around mixing, or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The catalyst co-promoter may be added as a non-iodide salt that will generate an iodide salt. The catalyst co-promoter may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding catalyst co-promoter. For additional detail regarding rhodium catalysis and iodide salt generation, see U.S. Pat. Nos. 5,001,259; 5,026,908; 5,144,068 and 7,005,541, which are incorporated herein by reference in their entireties. The carbonylation of methanol utilizing iridium catalyst is well known and is generally described in U.S. Pat. Nos. 5,942,460, 5,932,764, 5,883,295, 5,877,348, 5,877,347 and 5,696,284, which are incorporated herein by reference in their entireties.

The halogen-containing catalyst promoter of the catalyst system may include an organic halide, such as an alkyl, aryl, and substituted alkyl or aryl halides. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide. In one embodiment, the methyl iodide concentration is maintained in the vapor product stream at a concentration from 24 wt. % to less than 36 wt. %. In one embodiment, the reaction medium may have methyl iodide concentration of 7 wt. % or less, e.g., from 4 to 7 wt. %.

The components of the reaction medium are maintained within defined limits to ensure sufficient production of acetic acid. The reaction medium contains a concentration of the metal catalyst, e.g., rhodium catalyst, in an amount from 200 to 3000 wppm, e.g., from 800 to 3000 wppm, or from 900 to 1500 wppm. The concentration of water in the reaction medium is maintained to be less than or equal to 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains water in an amount from 0.1 to 4.1 wt. %, e.g., from 0.1 to 3.1 wt. % or from 0.5 to 2.8 wt. %. The concentration of methyl iodide in the reaction medium is maintained to be from 3 to 20 wt. %, e.g., from 4 to 13.9 wt. %, or from 4 to 7 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 9 wt. %, or from 0.6 to 4.1 wt. %. These amounts are based on the total weight of the reaction medium. The concentration of acetic acid in the reaction medium is generally greater than or equal to 30 wt. %, e.g., greater than or equal to 40 wt. % or greater than or equal to 50 wt. %.

Lithium Acetate in Reaction Medium

In embodiments, the process for producing acetic acid further includes introducing a lithium compound into the reactor to maintain the concentration of lithium acetate in an amount from 0.3 to 0.7 wt. % in the reaction medium. Without being bound by theory lithium acetate in the reaction medium in these concentrations may reduce the methyl iodide in the reaction medium and thus allow for controlling the methyl iodide in the vapor stream to be less than 36 wt. % as described herein. Also the introduction of the lithium compound into the reactor helps to stabilize the rhodium catalyst and thus reduces the amount of methyl iodide in the reaction medium required for achieving the suitable activity. Without introducing the lithium compound, additional rhodium would be needed when the methyl iodide concentration in the reaction medium decreases.

In embodiments, an amount of the lithium compound is introduced into the reactor to maintain the concentration of hydrogen iodide in an amount from 0.1 to 1.3 wt. % in the reaction medium. In embodiments, the concentration of the rhodium catalyst is maintained in an amount from 200 to 3000 wppm in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present in the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

LiOAc+HI⇌LiI+HOAc        (I)

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than or equal to 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %.

In one embodiment, there is provided a process for producing acetic acid, comprising carbonylating a reactant feed stream comprising methanol, methyl acetate, dimethyl ether, or mixtures thereof in a reactor in the presence of water, rhodium catalyst, iodide salt and methyl iodide to form a reaction medium in a reactor, introducing a lithium compound into the reactor, maintaining a concentration of lithium acetate in the reaction medium in an amount from 0.3 to 0.7 wt. %, separating the reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %. The process further comprises distilling at least a portion of the vapor product stream in a first column to obtain an acetic acid product stream comprising acetic acid and hydrogen iodide in an amount of less than or equal to 300 wppm and obtain an overhead stream comprising methyl iodide, water and methyl acetate.

It has been discovered that an excess of lithium acetate in the reaction medium can adversely affect the other compounds in the reaction medium, leading to decrease productivity. Conversely, it has been discovered that a lithium acetate concentration in the reaction medium below 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

In some embodiments, the desired reaction rates are obtained even at low water concentrations by maintaining an ester concentration in the reaction medium of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously.

Carbonylation Reaction

The carbonylation reaction of methanol to acetic acid product may be carried out by contacting the methanol feed with gaseous carbon monoxide, bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide, the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, it is preferred that it is an iodide salt of a member of the group consisting of the metals of Group IA and Group IIA of the periodic table, as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

The reaction medium may also contain impurities that should be controlled to avoid byproduct formation. These impurities tend to concentrate in the vapor stream. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be less than or equal to 750 wppm, or e.g., less than or equal to 650 wppm, or less than or equal to 550 wppm, or less than or equal to 450 wppm, or less than or equal to 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and less than or equal to 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1 or from 9:1 to 2:1.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. The temperature of the reactor may be controlled and the carbon monoxide feed is introduced at a rate sufficient to maintain the desired total reactor pressure. Stream 113 comprising the liquid reaction medium exits reactor 105.

Gaseous purge stream 106 desirably is vented from the reactor 105 to prevent buildup of gaseous by-products and to maintain a set carbon monoxide partial pressure at a given total reactor pressure. In one embodiment, the gaseous stream 106 contains low amounts of hydrogen iodide of less than or equal to 1 wt. %, e.g., less than or equal to 0.9 wt. %, less than or equal to 0.8 wt. %, less than or equal to 0.7 wt. %, less than or equal to 0.5 wt. %. Hydrogen iodide in excess of these amounts may increase the duty on the scrubber to prevent hydrogen iodide from being purged. In one embodiment, using maintaining a concentration of lithium acetate in the reaction medium in an amount from 0.3 to 0.7 wt. % may also advantageously control the hydrogen iodide concentration in the reaction medium in an amount from 0.1 to 1.3 wt. %. Lowering the hydrogen iodide in the reaction medium may also advantageously lower the hydrogen iodide in the gaseous stream. The embodiments using lithium acetate in the reaction medium advantageously reduces hydrogen iodide and results in less hydrogen iodide being withdrawn to the flash vessel as well as less hydrogen in the gaseous stream.

This further embodiment may also comprise scrubbing the gaseous stream to remove hydrogen iodide from a purge stream. Typically the treatment system is a scrubber, stripper or absorber, such as a pressure-swing absorber.

In one embodiment a process is provided for producing acetic acid, comprising carbonylating a reactant feed stream comprising methanol, methyl acetate, dimethyl ether, or mixtures thereof in a reactor. The reactant feed stream form a reaction medium with water, rhodium catalyst, iodide salt and methyl iodide in the reactor. The process further comprises introducing a lithium compound into the reactor, maintaining a concentration of lithium acetate in the reaction medium in an amount from 0.3 to 0.7 wt. %, venting a gaseous stream from the reactor that comprises hydrogen iodide in an amount of less than 1 wt. %. The process further comprises separating the reaction medium in a flash vessel to form a liquid recycle stream and a vapor product stream, which comprises acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %. The process further comprises distilling at least a portion of the vapor product stream in a first column to obtain an acetic acid product stream comprising acetic acid and hydrogen iodide in an amount of less than or equal to 300 wppm and obtain an overhead stream comprising methyl iodide, water and methyl acetate.

The acetic acid production system preferably includes separation system 108, employed to recover the acetic acid and recycle metal catalyst, methyl iodide, methyl acetate, and other system components within the process. One or more of the recycle streams may be combined prior to being introduced into the reaction system, which comprises the reactor and flash vessel. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof.

The reaction medium is drawn off from the carbonylation reactor 105 at a rate sufficient to maintain a constant level therein and is provided to flash vessel 110 via stream 113. Reactor 105 and flash vessel 110, along with the associated pumps, vents, pipes, and values, comprise the reaction system. The flash separation may be carried out at a temperature from 80° C. to 280° C., under an absolute pressure from 0.25 to 10 atm, and more preferably from 100° C. to 260° C. and from 0.3 to 10 atm. In one embodiment, the flash vessel may operate under a reduced pressure relative to the reactor. In flash vessel 110, the reaction medium is separated in a flash separation step to obtain a vapor product stream 112 comprising acetic acid and methyl iodide, as described herein, and liquid recycle stream 111 comprising a catalyst-containing solution. The catalyst-containing solution may be predominantly acetic acid containing the rhodium and the iodide salt along with lesser quantities of methyl acetate, methyl iodide, and water and is recycled to the reactor, as discussed above. Prior to returning liquid recycle to the reactor, a slip stream may pass through a corrosion metal removal bed, such as an ion exchange bed, to remove any entrained corrosion metals, such as nickel, iron, chromium, and molybdenum, as described in U.S. Pat. No. 5,731,252, which is incorporated herein by reference in their entirety. Also, the corrosion metal removal bed may be used to remove nitrogen compounds, such as amines, as described in U.S. Pat. No. 8,697,908, which is incorporated herein by reference in their entirety.

The vapor product stream 112 is described above as comprising acetic acid in an amount from 45 to 75 wt. %, methyl iodide in an amount from 24 to less than 36 wt. %, methyl acetate in an amount of less than or equal to 9 wt. %, and water in an amount of less than or equal to 14 wt. %, based on the total weight of the vapor product stream. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. Vapor product stream 112 may comprise hydrogen iodide in an amount less than or equal to 1 wt. %, based on the total weight of the vapor product stream, e.g., less than or equal to 0.5 wt. %, or less than or equal to 0.1 wt. %.

Liquid recycle stream 111 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

In one embodiment a process is provided for producing acetic acid carbonylating a reactant feed stream comprising methanol, methyl acetate, dimethyl ether, or mixtures thereof in a reactor. The reactant feed stream forms a reaction medium in the presence of water, a rhodium catalyst, an iodide salt and a methyl iodide. The process further comprises separating the reaction medium in a flash vessel to form a liquid recycle stream. The liquid recycle stream comprises rhodium catalyst in an amount from 0.01 to 0.5 wt. %, lithium iodide in an amount from 5 to 20 wt. %, corrosion metals in an amount from 10 to 2500 wppm, acetic acid in an amount from 60 to 90 wt. %, methyl iodide in an amount from 0.5 to 5 wt. %, methyl acetate in an amount from 0.1 to 5 wt. %, water in an amount from 0.1 to 8 wt. %. The liquid recycle stream also comprises a vapor product stream comprising acetic acid in an amount from 45 to 75 wt. %, methyl iodide in an amount from 24 to less than 36 wt. %, methyl acetate in an amount of less than or equal to 9 wt. % methyl acetate, water in an amount of less than or equal to 15 wt. %, and hydrogen iodide in an amount of less than or equal to 1 wt. %, and distilling at least a portion of the vapor product stream in a first column to obtain an acetic acid product stream comprising acetic acid and hydrogen iodide in an amount of less than or equal to 300 wppm and obtain an overhead stream comprising methyl iodide, water and methyl acetate.

The respective flow rates of vapor product stream 112 and liquid recycle stream 111 may vary, and in one exemplary embodiment from 15% to 55% of the flow into flash vessel 110 is removed as vapor product stream 112, and from 45% to 85% of the flow is removed as liquid recycle stream 111. The catalyst-containing solution may be predominantly acetic acid containing the metal catalyst, e.g., rhodium and/or iridium, and the iodide salt along with lesser quantities of methyl acetate, methyl iodide, and water and is recycled to reactor 105, as discussed above. Prior to returning the liquid recycle stream to the reactor, a slip stream may pass through a corrosion metal removal bed, such as an ion exchange bed, to remove any entrained corrosion metals as described in U.S. Pat. No. 5,731,252, which is incorporated herein by reference in its entirety. Also, the corrosion metal removal bed may be used to remove nitrogen compounds, such as amines, as described in U.S. Pat. No. 8,697,908, which is incorporated herein by reference in its entirety.

In addition to acetic acid, methyl iodide and acetaldehyde, vapor product stream 112 also may comprise methyl acetate, water, hydrogen iodide, and other PRC's, e.g., crotonaldehyde. Dissolved gases exiting reactor 105 and entering flash vessel 110 comprise a portion of the carbon monoxide and may also contain gaseous by-products such as methane, hydrogen, and carbon dioxide. Such dissolved gases exit flash vessel 110 as part of the vapor product stream 112. In one embodiment, carbon monoxide in gaseous purge stream 106 may be fed to the base of flash vessel 110 to enhance rhodium stability.

Recovery of Acetic Acid

The distillation and recovery of acetic acid is not particularly limited for the purposes of the present invention. In one embodiment a process is provided for producing acetic acid, comprising separating a reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %, acetaldehyde in an amount from 0.005 to 1 wt. %, and hydrogen iodide in an amount less than or equal to 1 wt. %; distilling at least a portion of the vapor product stream in a first column to obtain an acetic acid product stream comprising acetic acid and hydrogen iodide in an amount of less than or equal to 300 wppm and an overhead stream comprising methyl iodide, water and methyl acetate; condensing the low boiling overhead vapor stream and biphasically separating the condensed stream to form a heavy liquid phase and a light liquid phase, and distilling the acetic acid product stream in a second column to obtain an acetic acid product.

First Column

As shown in FIG. 1, vapor product stream 112 comprising from 24 to less than 36 wt. % methyl iodide is directed to a first column 120, also referred to as a light ends column. In one embodiment, vapor product stream 112 comprises acetic acid, methyl acetate, water, methyl iodide, and acetaldehyde, along with other impurities such as hydrogen iodide and/or crotonaldehyde, and/or byproducts such as propionic acid. Distillation yields a low boiling overhead vapor stream 122, a purified acetic acid product that preferably is removed via a sidedraw stream 123, and a high boiling residue stream 121. A majority of the acetic acid is removed in sidedraw stream 123 and preferably little or no acetic acid is recovered from high boiling residue stream 121. Although the concentration of acetic acid may be relatively high in boiling residue stream 121, the mass flow of the boiling residue stream 121 relative to side stream 123 is very small. In embodiments, the mass flow of the boiling residue stream 121 is less than or equal to 0.75% of side stream 123, e.g., less than or equal to 0.55%, or less than or equal to 0.45%.

In one embodiment, low boiling overhead vapor stream 122 comprises water in amount greater than or equal to 5 wt. %, e.g., greater than or equal to 10 wt. %, or greater than or equal to 25 wt. %. In terms of ranges, the low boiling overhead vapor stream 112 may comprise water in an amount from 5 wt. % to 80 wt. %, e.g., from 10 wt. % to 70 wt. % or from 25 wt. % to 60 wt. %. Reducing the water concentration to less than 5 wt. % is generally not advantageous because it would result in a large acetic acid recycle stream back to the reaction system and increase the recycle stream throughout the entire purification system. In addition to water, low-boiling overhead vapor stream 122 may also comprise methyl acetate, methyl iodide, and carbonyl impurities, such as PRC's, which are preferably concentrated in the overhead vapor stream to be removed from acetic acid in sidedraw stream 123.

As shown, low-boiling overhead vapor stream 122 preferably is condensed and directed to an overhead phase separation unit, as shown by overhead decanter 124. Conditions are desirably maintained such that the condensed low-boiling overhead vapor stream 122, once in decanter 124, may separate and form a light liquid phase 133 and a heavy liquid phase 134. The phase separation should maintain two separate phases, without forming a third phase or emulsion between the phases. An offgas component may be vented via line 132 from decanter 124. In embodiments, the average residence time of the condensed low-boiling overhead vapor stream 122 in overhead decanter 124 is greater than or equal to 1 minute, e.g., greater than or equal to 3 minutes, greater than or equal to 5 minutes, greater than or equal to 10 minutes, and/or the average residence time is less than or equal to 60 minutes, e.g., less than or equal to 45 minutes, or less than or equal to 30 minutes, or less than or equal to 25 minutes.

Although the specific compositions of light liquid phase 133 may vary widely, some exemplary compositions are provided below in Table 1.

TABLE 1

Exemplary Light Liquid Phase from Light Ends Overhead

| | conc. (Wt. %) | conc. (Wt. %) | conc. (Wt. %) |
| --- | --- | --- | --- |
| Water | 40-80 | 50-75 | 70-75 |
| Methyl Acetate | 1-50 | 1-25 | 1-15 |
| Acetic Acid | 1-40 | 1-25 | 5-15 |
| PRC's (AcH) | <5 | <3 | <1 |
| Methyl Iodide | <10 | <5 | <3 |
| Hydrogen Iodide | <1 | <0.5 | 0.001-0.5 |

In one embodiment, overhead decanter 124 is arranged and constructed to maintain a low interface level to prevent an excess hold up of methyl iodide. Although the specific compositions of heavy liquid phase 134 may vary widely, some exemplary compositions are provided below in Table 2.

TABLE 2

Exemplary Heavy Liquid Phase from Light Ends Overhead

| | conc. (Wt. %) | conc. (Wt. %) | conc. (Wt. %) |
| --- | --- | --- | --- |
| Water | <3 | 0.05-1 | 0.01-1 |
| Methyl Acetate | 0.1-25 | 0.5-20 | 0.7-15 |
| Acetic Acid | 0.1-10 | 0.5-10 | 0.7-10 |

TABLE 2-continued

Exemplary Heavy Liquid Phase from Light Ends Overhead

|  | conc. (Wt. %) | conc. (Wt. %) | conc. (Wt. %) |
|---|---|---|---|
| PRC's (AcH) | <5 | <3 | 0.05-0.5 |
| Methyl Iodide | 60-98 | 60-95 | 80-90 |
| Hydrogen Iodide | <1 | <0.5 | 0.001-0.5 |

The density of the heavy liquid phase 134 may be from 1.3 to 2, e.g., from 1.5 to 1.8, from 1.5 to 1.75 or from 1.55 to 1.7. As described in U.S. Pat. No. 6,677,480, the measured density in the heavy liquid phase 134 may correlate to the methyl acetate concentration in the reaction medium. As density decreases, the methyl acetate concentration in the reaction medium increases. In one embodiment of the present invention, heavy liquid phase 134 is recycled to the reactor and the light liquid phase 133 is controlled to be recycled through the same pump. It may be desirable to recycle a portion of the light liquid phase 133 that does not disrupt the pump and to maintain a density of the combined light liquid phase 133 and heavy liquid phase of greater than or equal to 1.3, e.g., greater than or equal to 1.4, greater than or equal to 1.5, or greater than or equal to 1.7. As described herein, a portion of the heavy liquid phase 134 may be treated to remove impurities, such as acetaldehyde.

As indicated by Tables 1 and 2, the water concentration in the light liquid phase 133 is larger than the heavy liquid phase 134, and thus the present invention can control the side stream water concentration through the recycle of the light liquid phase. The concentration of components in sidedraw stream 123, such as water and/or hydrogen iodide, may be controlled by the recycle rate of light liquid phase 133 to the reaction system. The reflux ratio (the mass flow rate of the reflux divided by the total mass flow exiting the top of the column 120, including both heavy liquid phase 134, which may or may not be fully recycled, and light liquid phase 133) to the first column of the light liquid phase 133 via line 135 preferably is from 0.05 to 0.4, e.g., from 0.1 to 0.35 or from 0.15 to 0.3. In one embodiment, to reduce the reflux ratio, the number of theoretical trays above the sidedraw stream and top of first column may be greater than 5, e.g., preferably greater than 10. In one embodiment, to reduce the reflux ratio, the number of theoretical trays above the side stream and top of first column may be greater than or equal to 5, e.g., preferably greater than or equal to 10. In one embodiment, a flow valve and/or flow monitor (not shown) may be used to control the reflux in line 135 and recycle in line 136.

In one embodiment, the recycle of light liquid phase in line 136 back to reactor 105 is up to or equal to 20%, e.g., up to or equal to 10%, of the total light liquid phase 133 condensed from the column overhead (reflux plus recycle). In terms of ranges the recycle of light liquid phase in line 136 may be from 0 to 20%, e.g., from 0.1 to 20%, from 0.5 to 20%, from 1 to 15%, or from 1 to 10%, of the total light liquid phase 133, which is condensed from the low-boiling overhead vapor stream (reflux plus recycle). The remaining portion may be used as a reflux on the light ends column or fed to an PRC removal system. For example, recycle in line 136 may be combined with liquid recycle stream 111 and be returned to reactor 105. In one embodiment, recycle in line 136 may be combined with another stream that is being recycled to the reaction system, e.g., reactor 105 or flash vessel 110. When condensed overhead stream 138 from drying column 125 is phase-separated to form an aqueous phase and an organic phase, the recycle in line 136 may be preferably combined with the aqueous phase. Alternatively, recycle in line 136 may be combined, or at least partially combined, with heavy liquid phase 134 and/or the organic phase from the overhead stream 138.

PRC Removal System

Although not shown, a portion of light liquid phase 133 and/or heavy liquid phase 134 may be separated and directed to acetaldehyde or PRC removal system to recover methyl iodide and methyl acetate during the acetaldehyde removal process. As shown in Tables 1 and 2, light liquid phase 133 and/or heavy liquid phase 134 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 133 and/or heavy liquid phase 134 fed to the acetaldehyde or PRC removal system may vary from 1% to 99% of the mass flow of either the light liquid phase 133 and/or heavy liquid phase 134, e.g., from 1 to 50%, from 2 to 45%, from 5 to 40%, 5 to 30% or 5 to 20%. Also in some embodiments, a portion of both the light liquid phase 133 and heavy liquid phase 134 may be fed to the acetaldehyde or PRC removal system. The portion of the light liquid phase 133 not fed to the acetaldehyde or PRC removal system may be refluxed to the first column or recycled to the reactor, as described herein. The portion of the heavy liquid phase 134 not fed to the acetaldehyde or PRC removal system may be recycled to the reactor. Although a portion of heavy liquid phase 134 may be refluxed to the first column, it is more desirable to return the methyl iodide enriched heavy liquid phase 134 to the reactor.

In one embodiment, a portion of light liquid phase 133 and/or heavy liquid phase 134 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 134 is treated in the PRC removal system, it may be desirable to return a portion the raffinate to either the distillation column or reactor. Also, for example, when light liquid phase 133 is treated in the PRC removal system, it may be desirable to return a portion the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase 133, may also be recycled to reactor 105 and/or refluxed to first column 120.

In one embodiment, there is provided a process for producing acetic acid comprising carbonylating a reactant feed stream comprising methanol, methyl acetate, dimethyl ether, or mixtures thereof in a reactor in the presence of water, rhodium catalyst, iodide salt and methyl iodide to form a reaction medium in a reactor, introducing a lithium compound into the reactor, maintaining a concentration of lithium acetate in the reaction medium in an amount from 0.3 to 0.7 wt. %, separating the reaction medium in a flash vessel to form a liquid recycle stream, and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %. The method further comprises distilling at least a portion of the vapor product stream in a first column to obtain an acetic acid product stream comprising acetic acid and hydrogen iodide in an amount of less than or equal to 300 wppm and obtain an overhead stream comprising methyl iodide, water and methyl acetate; condensing the overhead stream and phase-separating the condensing overhead to form a light liquid phase and a heavy liquid phase; and treating a portion of the heavy liquid phase to remove at least one permanganate-reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof In some embodiments, the process includes one or more on-line analyzers for measuring the concentrations of various components in the various streams. For example, an on-line analyzer may be used to determine the hydrogen iodide concentration of sidedraw stream 123 by feeding a sample stream, e.g., a sample purge stream, to an on-line analyzer (not shown).

Second Column

Acetic acid removed via sidedraw stream 123 preferably is subjected to further purification, such as in a second column 125, also referred to as a drying column. The second column separates sidedraw stream 123 to form an aqueous overhead stream 126 comprising primarily water, and product stream 127 comprised primarily of acetic acid. Water from the side stream is concentrated in the aqueous overhead stream and the aqueous overhead comprises greater than or equal to 90% of the water in the side stream, e.g., greater than or equal to 95%, greater than or equal to 97%, greater than or equal to 99%. Aqueous overhead stream 126 may comprise water in an amount from 50 to 90 wt. %, e.g., from 50 to 85 wt. %, from 55 to 85 wt. %, from 60 to 80 wt. %, or from 60 to 75 wt. %. In embodiments, aqueous overhead stream may comprise water in an amount of less than or equal to 90 wt. %, e.g., less than or equal to 75 wt. %, less than or equal to 70 wt. %, less than or equal to 65 wt. %. Methyl acetate and methyl iodide are also removed from the side stream and concentrated in the overhead stream. Product stream 127 preferably comprises or consists essentially of acetic acid and may be withdrawn in the bottom of second column 125 or a side stream near the bottom. When withdrawn as a side stream near the bottom, the side stream may be a liquid or a vapor stream. In preferred embodiments, product stream 127 comprises acetic acid in an amount greater than or equal to 90 wt. %, e.g., greater than or equal to 95 wt. % or greater than or equal to 98 wt. %. Product stream 127 may be further processed, e.g., by passing through an ion exchange resin, prior to being stored or transported for commercial use.

Similarly, aqueous overhead stream 126 from second column 125 contains a reaction component, such as methyl iodide, methyl acetate, and water, and it is preferable to retain these reaction components within the process. Aqueous overhead stream 126 is condensed by a heat exchanger into stream 138, which is recycled to reactor 105 and/or refluxed second column 125. An offgas component may be vented via line 137 from condensed low-boiling overhead vapor stream 126. Similar to the condensed low-boiling overhead vapor stream from first column 120, condensed overhead stream 138 may also be separated to form an aqueous phase and an organic phase, and these phases may be recycled or refluxed as needed to maintain the concentrations in the reaction medium.

In one embodiment, the side stream water concentration is controlled to balance the water in both the first and second columns. When less than or equal to 14 wt. % water is used in the reaction medium, more preferably, less than or equal to 4.1 wt. % water there may not be sufficient water in the second column to stably operate the column. Although it may be possible to reduce the water concentration in the side stream to less than 1 wt. %, this would result in an imbalance in the second column, which may cause the recovery of acetic acid to become more difficult and therefore result in off-spec product. Further by having water in the side stream, the second column can remove that water in the aqueous overhead. The recycle ratio between the light liquid phase from the first column and the aqueous overhead from the second column helps to maintain desirable water concentrations in the reactor while maintaining stable operations in the first and second distillation columns. In one embodiment, the recycle ratio of the mass flow of the light liquid phase recycled to the reactor to the mass flow of the aqueous overhead to the reactor is less than or equal to 2, e.g., less than or equal to 1.8, less than or equal to 1.5, less than or equal to 1, less than or equal to 0.7, less than or equal to 0.5, less than or equal to 0.35, less than or equal to 0.25 and/or the recycle ratio of the mass flow of the light liquid phase recycled to the reactor to the mass flow of the aqueous overhead to the reactor is greater than or equal to 0, e.g., greater than or equal to 0.05, greater than or equal to 0.1, greater than or equal to 0.15, or greater than or equal to 0.2.

Thus, in one embodiment, there is provided a process for producing acetic acid comprising carbonylating a reactant feed stream in the presence of water, rhodium catalyst, iodide salt and methyl iodide to form a reaction medium in a reactor. The reactant feed stream comprises methanol, methyl acetate, dimethyl ether, or mixtures thereof. The process further comprises introducing a lithium compound into the reactor, maintaining a concentration of lithium acetate in the reaction medium in an amount from 0.3 to 0.7 wt. %; separating the reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, water in an amount of less than or equal to 14 wt. %; and distilling at least a portion of the vapor product stream in a first column to obtain an acetic acid product stream comprising acetic acid and hydrogen iodide in an amount of less than or equal to 300 wppm, and obtain an overhead stream comprising methyl iodide, water and methyl acetate, condensing the first low boiling overhead vapor stream and biphasically separating the condensed stream to form a heavy liquid phase and a light liquid phase; distilling the side stream in a second column to obtain a purified acetic acid product and a second low boiling overhead vapor stream; condensing the second low-boiling overhead vapor stream to obtain an aqueous recycle stream, comprising water in an amount of less than or equal to 90 wt. %; and recycling the second low boiling overhead vapor stream to the reactor, wherein the recycle ratio of the mass flow of the light liquid phase recycled to the reactor to the mass flow of the aqueous recycle stream to the reactor is less than or equal to 2, e.g., from 0 to 2.

To recover residual liquids from the vent stream, in particular lines 106, 132, and 137, these lines may be fed to a scrubber that operates with cooled methanol and/or acetic acid to remove methyl acetate and methyl iodide. A suitable scrubber is described in U.S. Pat. No. 8,318,977, which is incorporated herein by reference in its entirety.

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited, and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity, according to the composition of the feed stream. For example, in a case where the purification of acetic acid is carried out by the distillation column, the inner pressure of the distillation column (usually the pressure of the column top) may be from 0.01 to 1 MPa, e.g., from 0.02 to 0.7 MPa, and more preferably, from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

Guard Bed

A low total iodide concentration, e.g., up to 5 wppm, e.g., up to 1 wppm, in the purified acetic acid product, allows for removal of iodide using a guard bed. The use of one or more guard beds to remove residual iodide greatly improves the quality of the purified acetic acid product. Carboxylic acid streams, e.g., acetic acid streams, that are contaminated with halides and/or corrosion metals may be contacted with the ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with the ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

In one embodiment, the ion exchange resin is a metal-exchanged ion exchange resin and may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

The pressure during the contacting step is limited primarily by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably, the guard bed is configured in a position wherein the temperature acetic acid product stream is low, e.g., less than or equal to 120° C. or less than or equal to 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is up to 5 wppm, e.g., preferably up to 1 wppm. In one exemplary embodiment, the total iodide concentration of the purified acetic acid product may be from 0.01 wppm to 5 wppm, e.g., from 0.01 wppm to 1 wppm. Concentrations of iodide above 5 wppm may require re-processing the off-spec acetic acid. Total iodide concentration includes iodide from both organic, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than or equal to 100 wppb iodides, e.g., less than or equal to 90 wppb, less than or equal to 50 wppb, or less than or equal to 25 wppb. In one embodiment, the purified acetic acid composition comprises less than or equal to 1000 wppb corrosion metals, e.g., less than or equal to 750 wppb, less than or equal to 500 wppb, or less than or equal to 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

In another embodiment, the product stream may be contacted with cationic exchanger to remove lithium compounds. The cationic exchanger in the acid form comprises a resin of acid-form strong acid cation exchange macroreticular, macroporous or mesoporous resins. Without being bound by theory feeding a product stream to an ion-exchange comprising lithium compounds in an amount of greater than or equal to 10 wppm results in displacement of metals in the treated product. Advantageously, this may be overcome by using an cationic exchanger upstream of the ion-exchange resin. After contacting with the cationic exchanger, the product stream may have a lithium ion concentration of less than 50 weight part per billion (wppb), e.g., less than 10 wppb, or less than 5 wppb.

Although the product stream may be contacted with an ion-exchange resin to remove iodides, it is preferred not to flash the product stream or contact with product stream with an adsorption system that contains activated carbon. Flashing the product stream is not efficient because there is not a sufficient pressure drop to recover greater than 50% of the acetic acid from the product stream. Thus, in one embodiment, a non-flashed portion of the product stream is fed to the ion-exchange bed to remove iodides.

As is evident from the figures and text presented above, a variety of embodiments are contemplated.

E1. A process for producing acetic acid, comprising:
carbonylating a reactant feed stream comprising methanol, methyl acetate, dimethyl ether, or mixtures thereof in a reactor in the presence of water, rhodium catalyst, iodide salt and methyl iodide to form a reaction medium in a reactor;
introducing a lithium compound into the reactor;
maintaining a concentration of lithium acetate in the reaction medium in an amount from 0.3 to 0.7 wt. %;
separating the reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, and water in an amount of less than or equal to 14 wt. %; and
distilling at least a portion of the vapor product stream in a first column to obtain an acetic acid product stream comprising acetic acid and hydrogen iodide in an amount of less than or equal to 300 wppm and an overhead stream comprising methyl iodide, water and methyl acetate.

E2. The process of embodiment E1, wherein the vapor product stream further comprises acetaldehyde in an amount from 0.005 to 1 wt. %.

E3. The process of any one embodiments E1-E2, wherein the vapor product stream further comprises acetaldehyde in an amount from 0.01 to 0.8 wt. %.

E4. The process of any one embodiments E1-E3, wherein the vapor product stream comprises acetic acid in an amount from 55 to 75 wt. %, methyl iodide in an amount from 24 to 35 wt. %, methyl acetate in an amount from 0.5 to 8 wt. %, water in an amount from 0.5 to 14 wt. %, and further comprises hydrogen iodide in an amount less than or equal to 0.5 wt. %.

E5. The process of any one embodiments E1-E4, wherein the vapor product stream comprises acetaldehyde in an amount from 0.01 to 0.7 wt. %.

E6. The process of embodiment E5, wherein the vapor product stream comprises acetic acid in an amount from 60 to 70 wt. %, methyl iodide in an amount from 25 to 35 wt. %, methyl acetate in an amount from 0.5 to 6.5 wt. %, water in an amount from 1 to 8 wt. %, acetaldehyde in an amount from 0.01 to 0.7 wt. %, and hydrogen iodide in an amount less than or equal to 0.1 wt. %.

E7. The process of any one embodiments E1-E6, wherein the vapor product stream comprises hydrogen iodide in an amount less than or equal to 1 wt. %.

E8. The process of any one embodiments E1-E7, further comprising venting from the reactor a gaseous stream that comprises hydrogen iodide in an amount of less than or equal to 1 wt. %.

E9. The process of embodiment E8, wherein the gaseous stream comprises hydrogen iodide in an amount from 0.001 to 1 wt. %.

E10. The process of any one embodiments E1-E9, wherein the overhead stream is phase separated to form a light liquid phase and a heavy liquid phase.

E11. The process of embodiment E10, wherein the light liquid phase comprises acetic acid in an amount from 1 to 40 wt. %, methyl iodide in an amount of less than or equal to 10 wt. %, methyl acetate in an amount from 1 to 50 wt. %, water in an amount from 40 to 80 wt. %, acetaldehyde in an amount of less than or equal to 5 wt. %, and hydrogen iodide in an amount of less than or equal to 1 wt. %.

E12. The process of embodiment E10, wherein the light liquid phase comprises acetic acid in an amount from 5 to 15 wt. %, methyl iodide in an amount of less than or equal to 3 wt. %, methyl acetate in an amount from 1 to 15 wt. %, water in an amount from 70 to 75 wt. %, acetaldehyde in an amount from 0.1 to 0.7 wt. %, and hydrogen iodide in an amount from 0.001 to 0.5 wt. %.

E13. The process of embodiment E10, wherein a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof.

E14. The process of embodiment E10, wherein a portion of the light liquid phase is returned to the reactor.

E15. The process of any one embodiments E1-E14, wherein the liquid recycle stream comprises a rhodium catalyst in an amount from 0.01 to 0.5 wt. %, lithium iodide in an amount from 5 to 20 wt. %, corrosion metals in an amount from 10 to 2500 wppm, acetic acid in an amount from 60 to 90 wt. %, methyl iodide in an amount from 0.5 to 5 wt. %, methyl acetate in an amount from 0.1 to 5 wt. %, water in an amount from 0.1 to 8 wt. %, acetaldehyde in an amount from 0.0001 to 1 wt. %, and hydrogen iodide in an amount from 0.0001 to 0.5 wt. %.

E16. The process of any one embodiments E1-E15, wherein the lithium compound is selected from the group consisting of lithium acetates, lithium carboxylates, lithium carbonates, lithium hydroxides, and mixtures thereof.

E17. The process of any one embodiments E1-E16, further comprising maintaining a concentration of hydrogen iodide in the reaction medium in an amount from 0.1 to 1.3 wt. %.

E18. The process of any one embodiments E1-E17, wherein the carbonylation is conducted while maintaining a carbon monoxide partial pressure from 2 to 30 atm and a hydrogen partial pressure in the reactor that is less than or equal to 0.04 atm.

E19. The process of any one embodiments E1-E18, wherein the concentration of methyl acetate in the reaction medium is greater than the concentration of the lithium acetate in the reaction medium.

E20. The process of any one embodiments E1-E19, wherein the acetic acid product stream comprises each of the methyl iodide and the methyl acetate in an amount within the range of ±0.9 wt. % of the water concentration in the side stream.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

EXAMPLES

The present invention will be better understood in view of the following non-limiting examples.

Example 1

The reactor, containing approximately 900 ppm by weight of rhodium in the form of a rhodium carbonyl iodide compound and approximately 9 wt. % methyl iodide as well as lithium iodide, water, and methyl acetate, was fed with methanol, carbon monoxide and hydrogen to maintain a hydrogen partial pressure of at least about 0.27 atm (i.e. at least about 4 psi). The water concentration was less than 4 wt. %. The reactor maintained a temperature between about 190° C. and 200° C. and operated at a pressure above 28 atm (i.e. above 400 psig). By means of a level control sensing the liquid level within the reactor, liquid reaction medium was continuously withdrawn and fed to the a single-tray flash vessel operating at approximately 150° C. and approximately 3.2 atm (i.e. 32.3 psig). Carbon monoxide recovered from the reactor vent was spraged into the withdrawn reaction medium prior to entering the flash vessel. About 28% of reaction medium exits the as the vapor product stream and the remaining amount is returned as a liquid to the reactor. The vapor product stream was withdrawn at a temperature of approximately 50° C. The vapor product stream composition was as follows: 66.35 wt. % acetic acid, 25.01 wt. % methyl iodide; 5.97 wt. % methyl acetate, 1.53 wt. % water, 0.1 wt. % acetaldehyde, and less than 1 wt. % hydrogen iodide.

The vapor product stream was fed to a light ends column to obtain an overhead and a sidedraw stream. A typical example of the HI concentration in sidedraw stream was determined by titrating a sufficient amount of sidedraw stream sample with 0.01 M lithium acetate solution in 50 ml acetone. A pH electrode was used with Metrohm 716 DMS Titrino to determine the end point at Dynamic Equivalence-point Titration mode. HI concentration in wt. % was calculated based on the consumption of lithium acetate titrant as depicted in following equation.

$$HI\ wt.\ \% = \frac{(ml\ of\ LiOAc)(0.01M)(128\ g/mole) \times 100}{(g\ sample)(1000\ ml/L)}$$

A sample sidedraw stream composition having about 1.9 wt. % water, about 2.8 wt. % methyl iodide, and about 2.5 wt. % methyl acetate, was tested using this HI titration method. The HI concentrations varied from 50 wppm to 300 wppm, when there was a recycle of the light liquid phase from the overhead light ends to the reaction system. Thus, maintaining the methyl iodide concentration in the vapor product stream contributed to controlling the HI concentrations in the light ends column.

Example 2

The reaction of Example 1 was repeated except the methyl iodide in the reaction medium was approximately 12 wt. % and the pressure of the flash vessel was slightly lower, approximately 3.1 atm (i.e. 30.8 psig). About 31% of reaction medium exited as the vapor product stream and the remaining amount was returned as a liquid to the reactor. The vapor product stream composition was as follows: 61.97 wt. % acetic acid, 30.34 wt. % methyl iodide; 5.05 wt. % methyl acetate, 1.54 wt. % water, 0.09 wt. % acetaldehyde, and less than 1 wt. % hydrogen iodide.

A portion of the light liquid phase from the light ends overhead was recycled to the reaction system. The sidedraw stream contained 1.5 wt. % water, 3.6 wt. % methyl acetate, 2.1 wt. % methyl iodide, and less than 25 wppm HI, and the balance comprised acetic acid. HI concentrations were too low to measure directly with titration. The presence of other cations in the sidedraw made directly measuring HI difficult. The measure of total inorganic iodide, i.e., total possible maximized HI, was done directly. Other inorganic iodides may include lithium iodide, as well as corrosion metal iodide. Again, maintaining the methyl iodide concentration in the vapor product stream beneficially contributed to controlling the HI concentration in the light ends column and ultimately in the sidedraw stream.

What is claimed is:

1. A process for producing acetic acid, comprising:
    carbonylating a reactant feed stream comprising methanol, methyl acetate, dimethyl ether, or mixtures thereof in a reactor in the presence of water, rhodium catalyst, iodide salt and methyl iodide to form a reaction medium in a reactor;
    introducing a lithium compound into the reactor wherein the lithium compound is selected from the group consisting of lithium acetate, lithium carbonate, lithium hydroxide, and mixtures thereof;
    maintaining the concentration of lithium acetate in the reaction medium in an amount from 0.3 to 0.7 wt. %;
    separating the reaction medium in a flash vessel to form a liquid recycle stream and a vapor product stream comprising acetic acid in an amount from 45 to 75 wt. %, methyl iodide in an amount from 24 to less than 36 wt. %, methyl acetate in an amount of less than or equal to 9 wt. %, and water in an amount of less than or equal to 14 wt. %; and
    distilling at least a portion of the vapor product stream in a first column to obtain an acetic acid product stream comprising acetic acid and hydrogen iodide in an amount of less than or equal to 300 wppm and an overhead stream comprising methyl iodide, water and methyl acetate.

2. The process of claim 1, wherein the vapor product stream further comprises acetaldehyde in an amount from 0.005 to 1 wt. %.

3. The process of claim 1, wherein the vapor product stream further comprises acetaldehyde in an amount from 0.01 to 0.8 wt. %.

4. The process of claim 1, wherein the vapor product stream comprises acetic acid in an amount from 55 to 75 wt. %, methyl iodide in an amount from 24 to 35 wt. %, methyl acetate in an amount from 0.5 to 8 wt. %, water in an amount from 0.5 to 14 wt. %, and further comprises hydrogen iodide in an amount less than or equal to 0.5 wt. %.

5. The process of claim 1, wherein the vapor product stream comprises acetaldehyde in an amount from 0.01 to 0.7 wt. %.

6. The process of claim 5, wherein the vapor product stream comprises acetic acid in an amount from 60 to 70 wt. %, methyl iodide in an amount from 25 to 35 wt. %, methyl acetate in an amount from 0.5 to 6.5 wt. %, water in an amount from 1 to 8 wt. %, acetaldehyde in an amount from 0.01 to 0.7 wt. %, and hydrogen iodide in an amount less than or equal to 0.1 wt. %.

7. The process of claim 1, wherein the vapor product stream comprises hydrogen iodide in an amount less than or equal to 1 wt. %.

8. The process of claim 1, further comprising venting from the reactor a gaseous stream that comprises hydrogen iodide in an amount of less than or equal to 1 wt. %.

9. The process of claim 8, wherein the gaseous stream comprises hydrogen iodide in an amount from 0.001 to 1 wt. %.

10. The process of claim 1, wherein the overhead stream is phase separated to form a light liquid phase and a heavy liquid phase.

11. The process of claim 10, wherein the light liquid phase comprises acetic acid in an amount from 1 to 40 wt. %, methyl iodide in an amount of less than or equal to 10 wt. %, methyl acetate in an amount from 1 to 50 wt. %, water in an amount from 40 to 80 wt. %, acetaldehyde in an amount of less than or equal to 5 wt. %, and hydrogen iodide in an amount of less than or equal to 1 wt. %.

12. The process of claim 10, wherein the light liquid phase comprises acetic acid in an amount from 5 to 15 wt. %, methyl iodide in an amount of less than or equal to 3 wt. %, methyl acetate in an amount from 1 to 15 wt. %, water in an amount from 70 to 75 wt. %, acetaldehyde in an amount from 0.1 to 0.7 wt. %, and hydrogen iodide in an amount from 0.001 to 0.5 wt. %.

13. The process of claim 10, wherein a portion of the heavy liquid phase is treated to remove at least one permanganate reducing compound selected from the group consisting of acetaldehyde, acetone, methyl ethyl ketone, butylaldehyde, crotonaldehyde, 2-ethyl crotonaldehyde, 2-ethyl butyraldehyde, and the aldol condensation products thereof.

14. The process of claim 10, wherein a portion of the light liquid phase is returned to the reactor.

15. The process of claim 1, wherein the liquid recycle stream comprises a rhodium catalyst in an amount from 0.01 to 0.5 wt. %, lithium iodide in an amount from 5 to 20 wt. %, corrosion metals in an amount from 10 to 2500 wppm, acetic acid in an amount from 60 to 90 wt. %, methyl iodide in an amount from 0.5 to 5 wt. %, methyl acetate in an amount from 0.1 to 5 wt. %, water in an amount from 0.1 to 8 wt. %, acetaldehyde in an amount from 0.0001 to 1 wt. %, and hydrogen iodide in an amount from 0.0001 to 0.5 wt. %.

16. The process of claim 1, further comprising maintaining a concentration of hydrogen iodide in the reaction medium in an amount from 0.1 to 1.3 wt. %.

17. The process of claim 1, wherein the carbonylation is conducted while maintaining a carbon monoxide partial pressure from 2 to 30 atm and a hydrogen partial pressure in the reactor that is less than or equal to 0.04 atm.

18. The process of claim 1, wherein the concentration of methyl acetate in the reaction medium is greater than the concentration of the lithium acetate in the reaction medium.

* * * * *